United States Patent
Kaplan et al.

(10) Patent No.: US 11,229,726 B2
(45) Date of Patent: *Jan. 25, 2022

(54) BIODEGRADABLE SILK EAR TUBES

(71) Applicants: Tufts University, Medford, MA (US); Massachusetts Eye and Ear Infirmary, Boston, MA (US); The General Hospital Corporation, Boston, MA (US)

(72) Inventors: David Kaplan, Concord, MA (US); Michael Whalen, Needham, MA (US); Christopher Hartnick, Newton, MA (US)

(73) Assignees: Tufts University, Medford, MA (US); Massachusetts Eye and Ear Infirmary, Boston, MA (US); The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/220,914

(22) Filed: Apr. 1, 2021

(65) Prior Publication Data
US 2021/0220526 A1    Jul. 22, 2021

Related U.S. Application Data

(63) Continuation of application No. 15/746,141, filed as application No. PCT/US2016/043166 on Jul. 20, 2016.
(Continued)

(51) Int. Cl.
*A61L 29/14*  (2006.01)
*A61F 11/00*  (2006.01)
(Continued)

(52) U.S. Cl.
CPC .......... *A61L 29/148* (2013.01); *A61F 11/002* (2013.01); *A61L 29/048* (2013.01);
(Continued)

(58) Field of Classification Search
CPC ...... A61L 31/148; A61L 31/16; A61L 29/048; A61L 31/146; A61L 29/16; A61L 29/146;
(Continued)

(56) References Cited

U.S. PATENT DOCUMENTS

| 4,806,355 A | 2/1989 | Goosen |
| 5,015,476 A | 5/1991 | Cochrum |

(Continued)

FOREIGN PATENT DOCUMENTS

| WO | 9708315 A1 | 3/1997 |
| WO | 2006030182 A2 | 3/2006 |

(Continued)

OTHER PUBLICATIONS

Banani Kundu et al, ("Silk Fibroin biomaterials for tissue regenerations" in Advanced Drug Delivery Reviews 65 (2013) pp. 457-470). (Year: 2013).*

(Continued)

*Primary Examiner* — Blessing M Fubara
(74) *Attorney, Agent, or Firm* — Quarles & Brady, LLP

(57) ABSTRACT

In some embodiments, the present invention provides methods for making resorbable ear tubes including the steps of providing a silk fibroin solution, and forming a silk ear tube from the silk fibroin solution, wherein the silk ear tube is less than 2 mm in length and has an outer diameter of less than 1.5 mm, and wherein the silk ear tube is resorbable. In some embodiments, the present invention also provides methods for treating otitis media including the step of introducing a silk ear tube into the ear canal of a subject, wherein the silk ear tube is less than 2 mm in length and has an outer (Continued)

diameter of less than 1.5 mm, and wherein the silk ear tube is resorbed by the subject.

17 Claims, 10 Drawing Sheets

Related U.S. Application Data

(60) Provisional application No. 62/194,423, filed on Jul. 20, 2015.

(51) Int. Cl.
*A61L 29/04* (2006.01)
*A61L 29/16* (2006.01)

(52) U.S. Cl.
CPC ............. *A61L 29/146* (2013.01); *A61L 29/16* (2013.01); *A61F 2210/0004* (2013.01); *A61F 2210/0076* (2013.01); *A61F 2240/001* (2013.01); *A61F 2250/0067* (2013.01); *A61L 2400/08* (2013.01); *A61L 2420/02* (2013.01); *A61L 2430/14* (2013.01)

(58) Field of Classification Search
CPC ................. A61L 31/047; A61L 29/148; A61L 2300/406; A61P 27/16; A61P 29/00; A61P 31/00; A61F 11/002; A61F 2210/0076; A61F 2210/0004; C08L 89/00
See application file for complete search history.

(56) References Cited

U.S. PATENT DOCUMENTS

| | | | |
|---|---|---|---|
| 5,093,489 A | 3/1992 | Diamantoglou | |
| 5,245,012 A | 9/1993 | Lombari et al. | |
| 5,263,992 A | 11/1993 | Guire | |
| 5,270,419 A | 12/1993 | Domb | |
| 5,576,881 A | 11/1996 | Doerr | |
| 5,902,800 A | 5/1999 | Green | |
| 6,127,143 A | 10/2000 | Gunasekaran | |
| 6,245,537 B1 | 6/2001 | Williams et al. | |
| 6,267,776 B1 | 7/2001 | O'Connell | |
| 6,302,848 B1 | 10/2001 | Larson | |
| 6,310,188 B1 | 10/2001 | Mukherjee | |
| 6,325,810 B1 | 12/2001 | Hamilton et al. | |
| 6,337,198 B1 | 1/2002 | Levene et al. | |
| 6,372,244 B1 | 4/2002 | Antanavich et al. | |
| 6,379,690 B2 | 4/2002 | Blanchard et al. | |
| 6,387,413 B1 | 5/2002 | Miyata et al. | |
| 6,395,734 B1 | 5/2002 | Tang et al. | |
| 2012/0034291 A1* | 2/2012 | Amsden | B82Y 20/00 424/443 |
| 2014/0094733 A1* | 4/2014 | Clopp | A61M 27/002 604/8 |

FOREIGN PATENT DOCUMENTS

| | | | | |
|---|---|---|---|---|
| WO | 2009023615 A1 | 2/2009 | | |
| WO | WO-2014051524 A1 * | 4/2014 | ........... | A61L 29/148 |
| WO | 2015077556 A1 | 5/2015 | | |
| WO | WO-2017015387 A1 * | 1/2017 | ............. | A61L 29/16 |

OTHER PUBLICATIONS

Meinel et al. ("Silk based Biomaterials to heal critical sized femur defects" in Bone, 39 (2006), pp. 922-931). (Year: 2006).*
Cheng et al. ("On the strength of b-Sheet Crystallites of *Bombyx mori* silk fibroin" in the Journal of the Royal Society Interface, 2014, 1-8). (Year: 2014).*
European Patent Office, Extended European Search Report, EP 16828483.4, dated Feb. 28, 2019, 9 pages.
European Patent Office, Extended European Search Report, EP 21162347.5, dated Jul. 6, 2021, 11 pages.
Gil, et al., Mechanical Improvements to Reinforced Porous Silk Scaffolds, J Biomed Mater Res A, 2011, 99(1):16-28.
Japan Patent Office. Office Action for application JP2018-503476. dated Jun. 15, 2020. With translation.
Li, et al., Study on Porous Silk Fibroin Materials. II. Preparation and Characteristics of Spongy Porous Silk Fibroin Materials, Journal of Applied Polymer Science, 2001, 79:2192-2199.
Min, et al., Preparation and Characterization of Crosslinked Porous Silk Fibroin Gel, Sen'i Gakkaishi, 1998, 54(2):85-92.
Nazarov, et al., Porous 3-D Scaffolds from Regenerated Silk Fibroin, Biomacromolecules, 2004, 5:718-726.
Okovity, et al., Medicamental Therapy of Otitis Externa and Otitis Media, Vestn Otorinolaringol, 2012, 1:52-56.
PCT International Search Report and Written Opinion, PCT/US2016/043166, dated Oct. 13, 2016, 8 pages.
Rockwood, D. N., et al. "Materials fabrication from *Bombyx mori* silk fibroin." Nature protocols 6.10 (2011): 1612.
Yucel, et al., Silk-Based Biomaterials for Sustained Drug Delivery, Journal of Controlled Release, 2014, 190:381-397.

* cited by examiner (A)

(B)

(C)

---------- COLLAR LENGTH (A, DASHED YELLOW): 0.41 mm
– – – – – LENGTH COLLAR-COLLAR (A, DASHED BLUE): 1.74mm
---------- LENGTH TOTAL (A, RED DASHED): 2.6mm
========== INNER DIAMETER (B, RED SOLID): 0.82 mm
---------- OUTER DIAMETER (B, PURPLE DASHED): 3.13 mm

BIODEGRADABLE SILK EAR TUBES

CROSS-REFERENCE TO RELATED APPLICATIONS

This application is a continuation of U.S. patent application Ser. No. 15/746,141, filed Jan. 19, 2018, and entitled "Biodegradable Silk Ear Tubes," which is a U.S. National Phase of PCT Application No. PCT/US2016/043166, filed Jul. 20, 2016, and entitled "Biodegradable Silk Ear Tubes," which claims the benefit of U.S. Provisional patent Application No. 62/194,423, filed Jul. 20, 2015, and entitled "Biodegradable Silk Ear Tubes," each of which are incorporated herein by reference in their entirety.

BACKGROUND

Tympanostomy tubes are small tubes inserted into the eardrum in order to keep the middle ear aerated and to prevent the buildup of fluid in the middle ear. Tympanostomy tube placement is the single most common ambulatory surgical procedure performed under general anesthesia in children, with 667,000 procedures done annually in the United States, often as a treatment for otitis media or barotrauma. At approximately $2,700 per procedure, the total financial burden is approximated at nearly $1.8 billion dollars, excluding perioperative visits and additional testing. By age 3, nearly 7% of children will have tubes in place. Unfortunately, previous tympanostomy tubes have proven unsatisfactory for a variety of reasons including triggering of chronic inflammation and scarring, and the need to conduct repeated surgical interventions.

SUMMARY

Unlike previous attempts at producing tympanostomy tubes (also referred to as "ear tubes"), the present invention provides for bioresorbable tubes that do not result in a substantial inflammatory reaction in a subject, and can be produced with any of a variety of physical and mechanical characteristics. For example, according to various embodiments, provided silk ear tubes may be produced to last for weeks, months, or years in a subject before being resorbed into the patient's body. Also, in some embodiments, provided silk ear tubes include multiple layers, each of which may include one or more of: pores, therapeutic agents, and varying mechanical and/or physical properties. In some embodiments, provided silk ear tubes may also have varying compositions and/or properties along their length. In some embodiments, provided silk ear tubes may comprise flanges, bevels, and/or other features.

In some embodiments, the present invention provides methods for making resorbable ear tubes including the steps of providing a silk fibroin solution, and forming a silk ear tube from the silk fibroin solution, wherein the silk ear tube is less than 2 mm in length and has an outer diameter of less than 1.5 mm, and wherein the silk ear tube is resorbable.

In some embodiments, the present invention also provides methods for treating otitis media including the step of introducing a silk ear tube into the ear canal of a subject, wherein the silk ear tube is less than 2 mm in length and has an outer diameter of less than 1.5 mm, and wherein the silk ear tube is resorbed by the subject. In some embodiments, the otitis media is acute otitis media, otitis media with effusion, or chronic suppurative otitis media.

According to various embodiments, provided silk ear tubes may be formed via any known method. In some embodiments, provided silk ear tubes are formed via gel spinning or gel deposition. In some embodiments, provided silk ear tubes are formed via dip coating or solution deposition. In some embodiments, provided silk ear tubes are formed via injection molding, micromolding, or machining.

In some embodiments, provided methods may allow for silk ear tubes comprising multiple layers. In some embodiments, the silk ear tube comprises at least two layers (e.g., at least 3, 4, 5, 6, 7, 8, 9, 10 or more layers). In some embodiments, provided silk ear tubes comprise a single layer.

In some embodiments, provided methods comprise one or more additional steps, for example, to conform particular silk ear tube(s) to a particular application and/or subject. In some embodiments, provided methods further comprise introducing a plurality of pores into at least one layer of provided silk ear tubes. In some embodiments, pores are introduced by associating a porogen with the silk fibroin solution prior to forming the silk ear tube. In some embodiments, the porogen is selected from polyethylene oxide, NaCl, alkali metals, alkali earth metal halides, phosphates, sulfates, sugar crystals, water-soluble microspheres, polysaccharides, protein microspheres, wax particles, and synthetic polymer particles. In some embodiments, pores are introduced using other known methods, for example, lyophilization or gas evolution methods.

According to various embodiments, one or more properties of the silk fibroin solution may be varied including, but not limited to the amount of silk fibroin in the silk fibroin solution, the presence or absence of additional materials in the silk fibroin solution, and the composition of the solvent in the silk fibroin solution, to name just a few. For example, in some embodiments, the silk fibroin solution contains between 1%-30% wt silk fibroin in water. In some embodiments, the silk fibroin solution may also contain one or more other additives including, for example, glycerol and/or glycol. In some embodiments, the addition of one or more additives may be useful in controlling the formation and/or morphology of provided silk ear tubes.

In some embodiments, silk ear tubes used in provided methods comprise at least one therapeutic agent. In some embodiments, provided methods may further comprise associating at least one therapeutic agent with the silk fibroin solution prior to of during formation of the silk ear tube. In some embodiments, provided methods further comprise administering at least one therapeutic agent to the subject prior to introduction of the silk ear tube. In some embodiments, provided methods further comprise administering at least one therapeutic agent to the subject subsequent to introduction of the silk ear tube. In some embodiments, provided methods further comprise administering at least one therapeutic agent to the subject substantially concurrently with introduction of the silk ear tube. In some embodiments, the at least one therapeutic agent is selected from the group consisting of antibiotics, pain relievers, and steroids.

According to various embodiments, provided silk ear tubes are resorbable in a subject (i.e., are broken down and assimilated into a subject's body). In some embodiments, the silk ear tube has a resorption rate of between one day and one week, inclusive. In some embodiments, the silk ear tube has a resorption rate of between eight days and 2 years, inclusive.

It is contemplated that one or more physical properties of provided silk ear tubes may be varied in order to suit a specific application and/or subject's needs. For example, in some embodiments, provided silk ear tubes comprise substantial beta-sheet content. In some embodiments, the substantial beta sheet content is introduced by at least one of autoclaving, water vapor annealing and treatment with methanol. In some embodiments, beta-sheet content may be between 1-75% (e.g., 1-10%, 1-20%, 1-30%, 1-40%, 1-50%, 1-60%, 10-20%, 10-30%, 10-40%, 10-50%, 10-60%, 20-60%, 20-50%, 20-40%, 20-30%, or 0-60%). Without wishing to be held to a particular theory, it is contemplated that a higher beta-sheet content will lead to a slower degradation of provided silk ear tubes in vivo. In some embodiments, the beta-sheet content of provided silk ear tubes may vary in any application-appropriate manner. For example, in some embodiments, provided silk ear tubes may comprise a gradient of beta-sheet content. In some embodiments, a gradient may comprise a multi-layered silk ear tube with at least one layer having a beta-sheet content that is different (e.g., higher or lower) than at least one other layer.

According to various embodiments, any silk fibroin may be used in provided methods and silk ear tubes. In some embodiments, the silk fibroin is selected from the group consisting of spider silk (e.g., from *Nephila ciavipes*), silkworm silk (e.g., from *Bombyx mori*), and recombinant silks from silkworm or spider silks.

Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" are used as equivalents and may be understood to permit standard variation as would be understood by those of ordinary skill in the art; and (v) where ranges are provided, endpoints are included.

Agent: The term "agent" as used herein may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide, genetic signature, metabolite, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biocompatible: The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

Biodegradable: As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

Combination therapy: As used herein, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens.

Composition: A "composition" or a "pharmaceutical composition" according to this invention refers to the combination of two or more agents as described herein for co-administration or administration as part of the same regimen. It is not required in all embodiments that the combination of agents result in physical admixture, that is, administration as separate co-agents each of the components of the composition is possible; however many patients or practitioners in the field may find it advantageous to prepare a composition that is an admixture of two or more of the ingredients in a pharmaceutically acceptable carrier, diluent, or excipient, making it possible to administer the component ingredients of the combination at the same time.

Improve, increase or reduce: as used herein or grammatical equivalents thereof, indicate values that are relative to a baseline measurement, such as a measurement in the same individual prior to initiation of a treatment described herein, or a measurement in a control individual (or multiple control individuals) in the absence of the treatment described herein. In some embodiments, a "control individual" is an individual afflicted with the same form of disease or injury as an individual being treated.

Subject: By "subject" is meant a mammal (e.g., a human). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

DETAILED DESCRIPTION OF CERTAIN EMBODIMENTS

Figure 1:
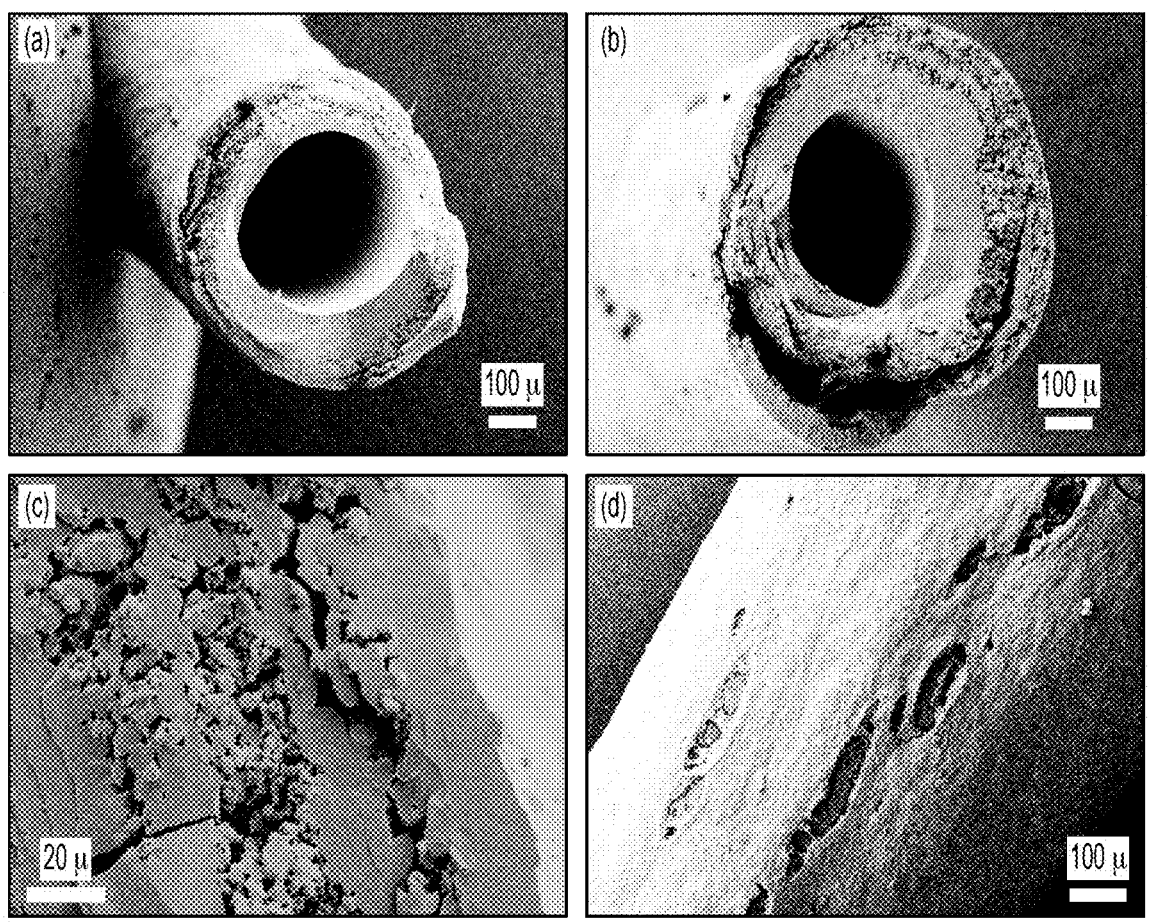
FIG. 1 shows images of silk tubes generated using dip-coating. (panel a) Dip-coated for 3 times, (panels b-d) dip-coated for 5 times, (panels a,b) fractured cross-section, (panel c) magnified fractured cross-section, (panel d) side view.

The present invention provides, inter alia, resorbable silk ear tubes with highly customizable physical and mechanical properties, as well as methods of making and using provided silk ear tubes.

According to various embodiments, the present invention provides methods for making resorbable ear tubes including the steps of providing a silk fibroin solution, and forming a silk ear tube from the silk fibroin solution, wherein the silk ear tube is less than 2 mm in length and has an outer diameter of less than 1.5 mm, and wherein the silk ear tube is resorbable. In some embodiments, provided silk ear tubes are substantially completely resorbable. In some embodiments, provided silk ear tubes are only partially resorbable.

Silk Fibroin Solutions

The silk fibroin solutions used in methods and compositions described herein may be obtained from a solution containing a dissolved silkworm silk, such as, for example, from *Bombyx mori*. Alternatively, the silk fibroin solution may be obtained from a solution containing a dissolved spider silk, such as, for example, from *Nephila clavipes*. The silk fibroin solution can also be obtained from a solution containing a genetically engineered silk such as from bacteria, yeast, mammalian cells, transgenic animals or transgenic plants. See, for example, WO 97/08315 and U.S. Pat. No. 5,245,012. In some embodiments, genetically engineered silk can, for example, comprise a therapeutic agent, e.g., a fusion protein with a cytokine, an enzyme, or any number of hormones or peptide-based drugs, antimicrobials and related substrates.

According to various embodiments, the silk fibroin solution can be prepared by any conventional method known to one skilled in the art. In some embodiments, the solution is an aqueous solution. For example, *B. mori* cocoons are boiled for about 30 minutes in an aqueous solution. In some embodiments, the aqueous solution is about 0.02M $Na_2CO_3$. The cocoons may be rinsed, for example, with water to extract the sericin proteins and the extracted silk is dissolved in an aqueous salt solution. Exemplary salts useful for this purpose include lithium bromide, lithium thiocyanate, calcium nitrate or other chemicals capable of solubilizing silk. Preferably, in some embodiments, the extracted silk is dissolved in about 9-12 M LiBr solution. The salt is consequently removed using, for example, dialysis.

If necessary, the solution can then be concentrated using, for example, dialysis against a hygroscopic polymer, for example, PEG, a polyethylene oxide, amylose or sericin. Preferably, the PEG is of a molecular weight of 8,000-10,000 g/mol and has a concentration of 25-50%. A slide-a-lyzer dialysis cassette (Pierce, MW CO 3500) is preferably used. However, any dialysis system can be used. The dialysis is for a time period sufficient to result in a final concentration of aqueous silk solution between 10-30%. In most cases dialysis for 2-12 hours is sufficient.

In accordance with various embodiments, a silk solution may comprise any of a variety of concentrations of silk fibroin. In some embodiments, a silk solution may comprise 0.1 to 40% by weight silk fibroin. In some embodiments, a silk solution may comprise between about 0.5% and 40% (e.g., 0.5% to 25%, 0.5% to 20%, 0.5% to 15%, 0.5% to 10%, 0.5% to 5%, 0.5% to 1.0%) by weight silk fibroin, inclusive. In some embodiments, a silk solution may comprise between 15-30% (e.g., 20-25%) by weight silk fibroin, inclusive. In some embodiments, a silk solution may comprise at least 0.1% (e.g., at least 0.5%, 1%, 2%, 3%, 4%, 5%, 6%, 7%, 8%, 9%, 10%, 15%, 20%, 25%, 30%, 35%, 40%) by weight silk fibroin. In some embodiments, a silk solution may comprise at most 30% (e.g., at most 40%, 35%, 30%, 25%, 20%, 15%, 14%, 13%, 12% 11%, 10%, 5%, 4%, 3%, 2%, 1%) by weight silk fibroin In some embodiments, the silk ear tube compositions described herein, and the methods using them can be performed in the absence of any organic solvent. Thus, these compositions and methods are particularly amenable to the incorporation of labile molecules, such as bioactive agents or therapeutics, and can, in certain embodiments, be used to produce controlled release biomaterials. Preferably, the methods are performed in water only.

Alternatively, in some embodiments, the silk fibroin solution can be produced using organic solvents, for example hexafluoroisopropanol (HFIP). Such methods have been described, for example, in Li, M., et al., J. Appi. Poly Sci. 2001, 79, 2192-2199; Mm, s., et al. Sen I Gakkaishi 1997, 54, 85-92; Nazarov, R. et al., Biomacromolecules 2004 May-June; 5(3):71 8-26.

In some embodiments, non-silk biocompatible polymers can also be added to the silk solution to generate composite matrices in the silk ear tubes described herein. Biocompatible polymers useful in the compositions described herein include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S.

Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). In some embodiments, two or more biocompatible polymers can be used.

Dimensions

The outer diameter of provided silk ear tubes can vary according to the needs of a specific application and/or subject, for example, from about 0.1 mm to about 4 mm or more. As described herein, in some embodiments, silk ear tubes or constructs of specific inner lumen diameters may be prepared by using a rod of the desired diameter in the process of making silk ear tubes. Specific sizes include, for example, 0.1 mm, 0.2 mm, 0.3 mm, 0.4 mm, 0.5 mm, 0.6 mm, 0.7 mm, 0.8 mm, 0.9 mm, 1.0 mm, 1.2 mm, 1.4 mm, 1.6 mm, 1.8 mm, 2.0 mm, 2.2 mm, 2.4 mm, 2.6 mm, 2.8 mm, 3.0 mm, 3.2 mm, 3.4 mm, 3.6 mm, and 3.8 mm. The preferred sizes can also be expressed as a range, e.g., 0.1 to 2.9 mm, 0.1 to 2.5 mm, 0.1 to 2 mm, 0.1 to 1.5 mm, 0.1 to 1 mm, 1.0 to 3 mm, 1.0 to 2 mm, 1.0 to 1.5 mm, etc. In some embodiments, provided embodiments may vary from one or more of these values by at most 20% (e.g., at most 15%, 10%, 5%).

The length of provided silk ear tubes may also vary in an application and/or subject-specific manner. In some embodiments, provided silk ear tubes may have a length between 0.5 and 3 mm (e.g., between 0.5 and 2.5 mm, 0.5 and 2 mm, 0.5 and 1 mm, 1 and 2.5 mm, 1 and 2 mm, 1 and 1.5 mm). Specific lengths include, for example, 0.1 mm, 0.2 mm, 0.3 mm, 0.4 mm, 0.5 mm, 0.6 mm, 0.7 mm, 0.8 mm, 0.9 mm, 1.0 mm, 1.2 mm, 1.4 mm, 1.6 mm, 1.8 mm, 2.0 mm, 2.2 mm, 2.4 mm, 2.6 mm, 2.8 mm, and 3.0 mm. In some embodiments, provided embodiments may vary from one or more of these values by at most 20% (e.g., at most 15%, 10%, 5%).

As used herein, concentrations, amounts, sizes, porosities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a range of about 1.0 to about 3.0 mm should be interpreted to include not only the explicitly recited size limits of 1.0 to about 3.0 mm, but also to include individual dimensions such as 1.4 mm, 1.8 mm, 2.0 mm, and 2.7 mm, as well as sub-ranges such as 1.0-1.4 mm, 1.0-1.8 mm, 1.8-2.4 mm, 1.4-3.0 mm, etc. Further, such an interpretation should apply regardless of the breadth of the range or the characteristic being described, such as protein concentration, tubular porosity, lumen diameter, porogen concentration and amounts and concentrations of other ingredients or agents.

According to various embodiments, provided silk ear tubes may vary in shape in any of a variety of ways. For example, in some embodiments, provided silk ear tubes may comprise beveled edges on one or both ends, comprise one end that has a larger outer diameter than the other end, comprise one or more flanges, and/or comprises a smooth inner surface and a porous outer surface.

Layers

According to various embodiments, provided silk ear tubes may comprise two or more layers. In some embodiments, the thickness of each deposited layer can also be controlled, inter alia, by adjusting the concentration of fibroin in the silk fibroin solution used to form the layer. For example, in embodiments where provided silk ear tubes are formed through dip coating, the more concentrated the fibroin in the aqueous silk fibroin solution is, the more fibroin that is deposited on the rod or on the previous layer of silk fibroin and a more compact structure is formed.

In some embodiments, each layer of a silk ear tube has a substantially similar thickness and/or functionalization. In some embodiments, at least one layer of a silk ear tube has a thickness and/or functionalization that is different form at least one other layer. According to various embodiments, functionalization may include the addition of one or more therapeutic agent.

In some embodiments, a silk ear tube may have between 1 and 10 layers (e.g., between 1 to 9, 1 to 8, 1 to 7, 1 to 6, 1 to 5, 1 to 4, 1 to 3, or 1 to 2 layers). In some embodiments, provided silk ear tubes comprise a single layer. In some embodiments, each layer of a silk ear tube may be between 1 nanometer (nm) and 1 millimeter (mm). For example, in some embodiments, each layer of a silk ear tube may be between 10 nm and 1 mm (e.g., between 25 nm and 1 mm, 50 nm and 1 mm, 100 nm and 1 mm, 200 nm and 1 mm, 30 nm and 1 mm, 400 nm and 1 mm, 500 nm and 1 mm, or 600 nm and 1 mm). In some embodiments, each layer of a silk ear tube may be between 10 nm and 1 mm (e.g., between 10 nm and 900 nm, 10 nm and 800 nm, 10 nm and 700 nm, 10 nm and 500 nm, 10 nm and 400 nm, 10 nm and 300 nm, or 10 nm and 200 nm).

Pores

In some embodiments, provided silk ear tubes may be made porous through the use of one or more porogens. It is contemplated that any known porogen may be suitable for use according to various embodiments. In some embodiments, a porogen may be or comprise crystals (e.g., sodium chloride crystals, sugar crystals), micro- and/or nano-spheres, polymers (such as polyethylene oxide, or PEO), ice crystals, sulfates, phosphates, alkali metals, alkali earth metal halides, polysaccharides, wax particles, synthetic polymer particles, and/or a laser. In some embodiments a porogen may comprise mechanical introduction of pores (e.g., using a needle or other article or device to pierce a silk ear tube one or more times, or using stress to introduce one or more tears in the silk ear tube).

As used herein, the term "porous" refers to the property of at least one layer of a silk ear tube described herein to permit the passage of materials through the wall of the tube (in contrast to their passage through or along the lumen of the tube). Silk ear tubes described herein may encompass a range of porosities, from those that do not substantially permit the passage of cells or proteins, to those that substantially permit the passage of proteins, but not cells, to those that permit the passage of both. As used herein, the term "not porous" means that a tube as described herein does not substantially permit the passage of Alexa-Fluor-488-labeled BSA through the wall of the tube over the course of a 20 minute assay. By "not substantially permit" is meant that under the detection conditions described herein, no labeled BSA from inside the tube is detected outside the tube after a 20 minute assay. Alternatively, the porosity of a tubular composition as described herein can be expressed in terms of a permeability coefficient, measured/calculated as described herein or otherwise known in the art. Tubular compositions as described herein are considered "not porous" to the passage of proteins or cells if the permeability coefficient for Alexa-Fluor-488-labeled BSA is $7.3 \times 10^{-4} \pm 1.5 \times 10^{-4}$ cm/s or lower. As used herein, the term "permeable to proteins" means that a tubular composition as described herein permits the passage of Alexa-Fluor-488-labeled BSA through the tube wall with a permeability coefficient, measured as described herein, of at least $8.9 \times 10^{-4}$ cm/s. Other modes of assessment of porosity may include Scanning Electron Microscopy assessment of cross sections of provided silk ear tubes followed by image processing; or mercury porisimetry measurements.

Various embodiments may comprise silk ear tubes comprising pores of various sizes. In some embodiments, pores in a silk ear tube may have a diameter between about 1-100 µm, inclusive. In some embodiments, pores in a silk ear tube may have a diameter between about 1-50 µm (e.g., 1-40, 1-35, 1-30, 1-25, 1-20, 1-15 µm), inclusive. In some embodiments, pores in a silk ear tube may have a diameter between about 5-25 µm, inclusive. In some embodiments, pores in a silk ear tube may have a diameter between about 1-10 µm, inclusive.

Methods of Forming Silk Ear Tubes

According to various embodiments, provided silk ear tubes may be formed via any application-appropriate method. In some embodiments, for example, methods of making provided silk ear tubes include, but are not limited to, injection molding, dip coating, gel spinning, 3D printing, and machining, layer by layer techniques, and filling molds. Additionally, certain exemplary methods for forming silk ear tubes are shown in the Examples below.

In some embodiments, provided silk ear tubes as described herein may be sterilized using conventional sterilization process such as radiation based sterilization (i.e. gamma-ray), chemical based sterilization or autoclaving. In some embodiments, the sterilization process may be with ethylene oxide at a temperature between 52-55° C. for a time of 8 hours or less. In some embodiments, provided silk ear tubes may be sterilized via autoclaving using high temperature and pressure. After sterilization the biomaterials may be packaged in an appropriate sterilized moisture resistant package for shipment.

Therapeutic Agents

In some embodiments, provided silk ear tubes comprise one or more therapeutic agents. In some embodiments, the silk fibroin solution may be contacted with a therapeutic agent prior to forming the silk ear tube, or can be loaded onto the silk ear tube after it is formed (e.g., as a coating). In some embodiments, at least one therapeutic agent is entrapped in the silk during formation of the silk ear tube, for example, in some embodiments, drying of an aqueous fibroin layer with a stream of gas, e.g., dehydrating a silk fibroin layer with $N_2$ gas induces a conformation change of the fibroin to the beta sheet structure, which entraps the agent. In some embodiments, additional layers may then be added either with the same agent, a different agent, or no agent. In some embodiments, this stepwise deposition approach also allows entrapment of varied concentrations of therapeutics within each layer. According to various embodiments, any pharmaceutical carrier may optionally be used that does not dissolve the silk material. In some embodiments, a therapeutic agents may be present as a liquid, a finely divided solid, or any other appropriate physical form.

The variety of different therapeutic agents that can be used in conjunction with the silk ear tubes of the present invention is vast and includes small molecules, proteins, peptides and nucleic acids. In general, therapeutic agents which can be associated with tubular compositions described herein include, without limitation: anti-infectives such as antibiotics (e.g., ciprofloxacin) and antiviral agents; anti-rejection agents; analgesics and analgesic combinations; anti-inflammatory agents (e.g., dexamethasone); hormones such as steroids; growth factors (bone morphogenic proteins (i.e. BMP's 17), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β-III), vascular endothelial growth factor (VEGF)); nerve growth factors, anti-angiogenic proteins such as endostatin, and other naturally derived or genetically engineered proteins, polysaccharides, glycoproteins, or lipoproteins.

In some embodiments, provided silk ear tubes may comprise one or more proteases. In some embodiments a protease may be one or more of a serine protease (e.g., proteinase K, proteinase XIV, or α-chymotrypsin), collagenase, or a matrix metalloproteinase (MMP) (e.g., MMP_1, MMP-2, etc). In some embodiments, one or more proteases are embedded in the silk ear tube or are associated with the silk ear tube after implantation in a subject. In some embodiments, one or more proteases may be used that require one or more activating events in order to cause protease activation. In some embodiments an activating event may be, for example, hydration, change in pH (i.e., raising or lowering), the addition of a co-factor, and/or any other application-appropriate activating event. Additional information may be found in Brown et al., Impact of silk biomaterial structure on proteolysis, *Acta Biomaterialia,* 11:212-224, (2014), the disclosure of which is hereby incorporated in its entirety.

Methods of Use

One of skill in the art will be able to envision several uses for provided silk ear tubes. In some embodiments, the present invention provides methods for treating otitis media including the step of introducing a silk ear tube into the ear canal of a subject, wherein the silk ear tube is less than 2 mm in length and has an outer diameter of less than 1.5 mm, and wherein the silk ear tube is resorbed by the subject. In some embodiments, the otitis media is acute otitis media, otitis media with effusion and conductive hearing loss, or chronic suppurative otitis media.

Provided silk ear tubes provide several advantages over previous tympanostomy tubes including the prevention of many common complications of previous tympanostomy tubes and methods of insertion. Amongst the common complications of tympanostomy tubes are delayed extrusion of the tubes with the need for a subsequent second surgery to remove the tubes as well as tympanosclerosis and granulation tissue that can develop around non-extruded tubes. A more ominous complication is the development of an atrophic region of the tympanic membrane adjacent to the tympanostomy tube, and can in turn lead to cholesteatoma formation. Various embodiments of the present invention are able to reduce or eliminate one or more of these exemplary complications stemming, at least in part, from use of previously known tympanostomy tubes. In some embodiments, provided insertion or implantation of silk ear tubes does not result in an inflammatory reaction in a subject.

According to various embodiments, provided silk ear tubes may be designed to last in vivo or on a shelf for extended periods of time. For example, in some embodiments, provided silk ear tubes may be produced that maintain substantial integrity in vivo for a period of time between 6 months and 5 years, in other words, these exemplary silk ear tubes have a resorption rate of between 6 months and 5 years. In some embodiments, provided silk ear tubes may have a resorption rate between one day and one week, between eight days and two years, between one year and four years, between one year and three years, or between one year and two years. In some embodiments, provided silk ear tubes may be produced that are shelf stable for one year, two years, three years, four years, five years, or more.

Unless otherwise defined, all technical and scientific terms used herein have the same meaning as commonly understood by one of ordinary skill in the art. Although methods and materials similar or equivalent to those described herein can be used in the practice or testing of the invention, the preferred methods and materials are described below. All publications, patent applications, patents and other references mentioned herein are incorporated by reference. In addition, the materials, methods and examples are illustrative only and not intended to be limiting. In case of conflict, the present specification, including definitions, controls.

EXAMPLES

Example 1—Exemplary Dip Coating and Gel Spinning Methods

Preparation of silk solution—Silk solution may be generated from *Bombyx mori* silkworm cocoons according to the procedures described in previous studies. Cocoons of *B. mori* silkworm silk can be supplied by Tajima Shoji Co (Yokohama, Japan). Briefly, the cocoons are degummed in a boiled 0.02 M $Na_2CO_3$ (Sigma-Aldrich, St Louis, Mo.) solution for 20 min. The fibroin extract is then rinsed three times in Milli-Q water, dissolved in a 9.3-M LiBr solution yielding a 20% (w/v) solution, and subsequently dialyzed (MWCO 3,500) against distilled water for 2 days to obtain silk fibroin aqueous solution (ca. 8 wt/vol %).

Figure 2:
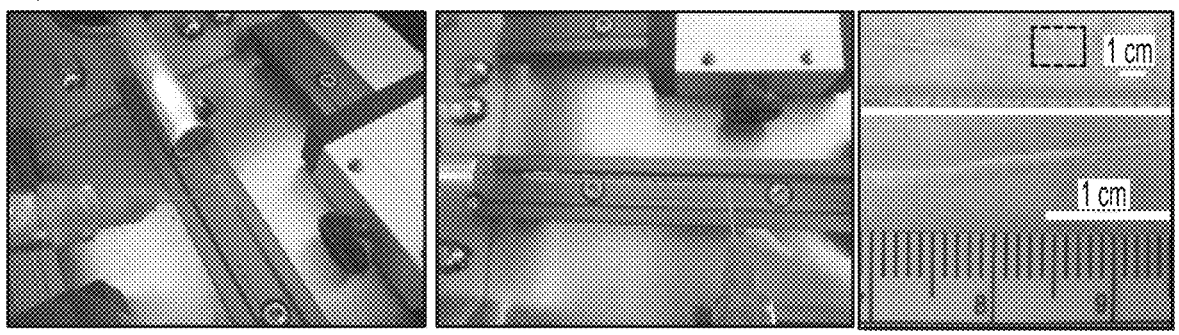
FIG. 2 shows portions of an exemplary fabrication process. (panel A) Digital pictures of the fabrication of gel spun silk tubes. In the left image, a polypropylene tube (1090 µm outer diameter) was assembled to make one end of tube with a larger inner lumen fitting. In the middle image, highly concentrated silk solution was spun on the rotating metal wire. In the right image, the gel spun silk tube was obtained after freeze-drying. (panel B) The schematic of the silk catheter. The other end of tube was capped with silk by dipping one end into concentrated silk solution and drying. (panel C) The pictures demonstrate that the gel spun tubes are flexible even when dried.
Figure 2:
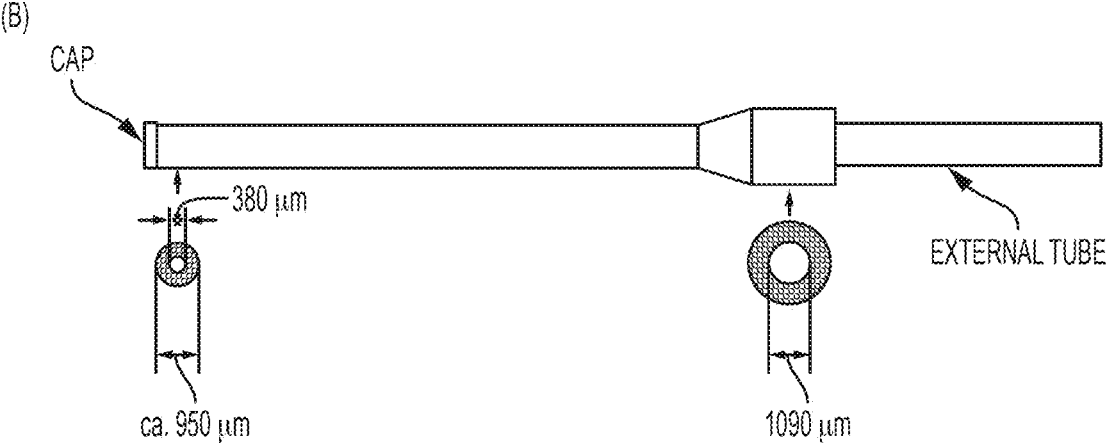
Figure 2:
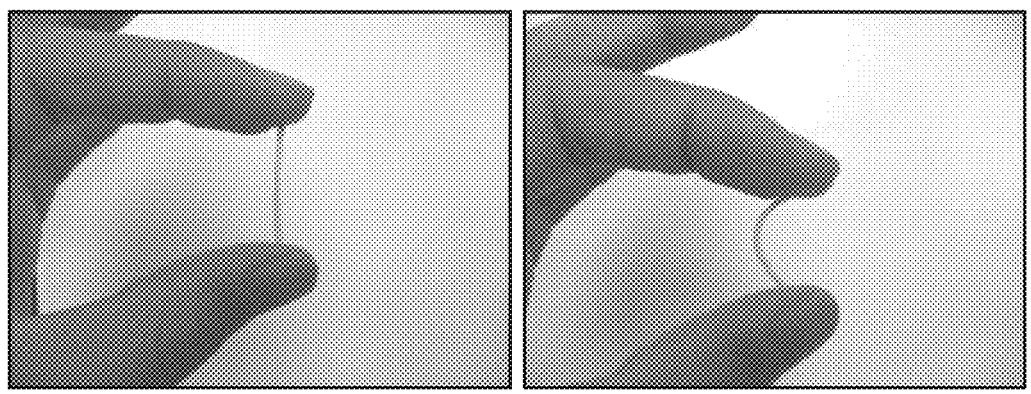

Preparation of silk tubes—In this Example, silk tubes are formed using exemplary multiple dip-coating or gel spinning methods. For the multiple dip-coating process, a mixture of silk fibroin (10 ml of 8 wt/vol %) and PEO (MW=900,000; Sigma-Aldrich) (4 ml of 5 wt/vol %) solution (Silk:PEO 4:1 w/w) is prepared (if pore formation within the silk tubular matrix is desired, if no pores are needed then the PEO need not be included in the process). Silk tubes are generated by dip-coating nitinol, Teflon or other wires or dowels (0.76 mm diameter) into the solution, treating the coated mixture solution on the wires or dowels in MeOH for 30 sec to stabilize the silk on the wire surface, and then drying the coated layer in air for 1 hour. This dipping process is repeated to generate around 1.36 mm outer diameter tubular matrices on the wires. Post-dip coating, the tubes are treated in MeOH for 2 hours and then placed into a water bath for 2 days to extract out the PEO (if used). The tubes are removed from the wire and dried in air. FIG. 1 shows exemplary images of silk ear tubes produced according to this dip coating method. For the gel spinning process, the silk solution is further concentrated (25-30 w/v %) by using a CentriVap vacuum concentrator (Labconco, Kansas City, Mo.). Tubular scaffolds are produced by spinning the concentrated silk solutions [25-30% (w/v), 0.1 ml/5 cm of scaffold] onto a rotating (200 rpm) and axially reciprocating wire with an axial slew rate (ASR) of 2 mm/sec using a custom gel spinning platform and program as described previously [10]. The tubes are lyophilized and treated with methanol for 2 hours and removed from the wires. FIG. 2 shows exemplary images and a schematic of silk ear tubes produced according to this gel-spinning method as well as some of the mechanical characteristics of such silk ear tubes (see panel C of FIG. 2).

Described in this Example are exemplary, non-limiting methods for producing silk fibroin solutions and forming silk ear tubes according to the present invention.

Example 2—Exemplary Production of Silk Ear Tubes Via Injection Molding

In this Example, silk ear tubes were produced using an injection molding process.

A mold was made of wax that was prepared from MachinableWax.com (USA) according to previously described methods. The molds were 3.30 cm in height and had a 0.76 cm diameter. The mold had two pieces, a 2 mm thick top piece that was placed on top of a 1 mm bottom wafer, providing supportive holes that were 0.76 mm in diameter corresponding the desirable placement of the PTFE in the top portion. The molds also had a thin wafer attached to a 6-well top piece, having a height of 0.25 cm. Prior to silk injection, the two pieces were placed on top of one another and sealed together with parafilm and the PTFE was secured in the middle of the well, via placement into the bottom-well socket. Next, 30 minute boil silk that was concentrated to 25-33 w/v % using the CentriVap bench top vacuum was loaded into each well of the mold. Following silk addition to the well, the mold was placed in $-20°$ C. for 4 hours and then placed in a lyophilizer on vacuum at $-30°$ C. until completely dry.

Figure 3:
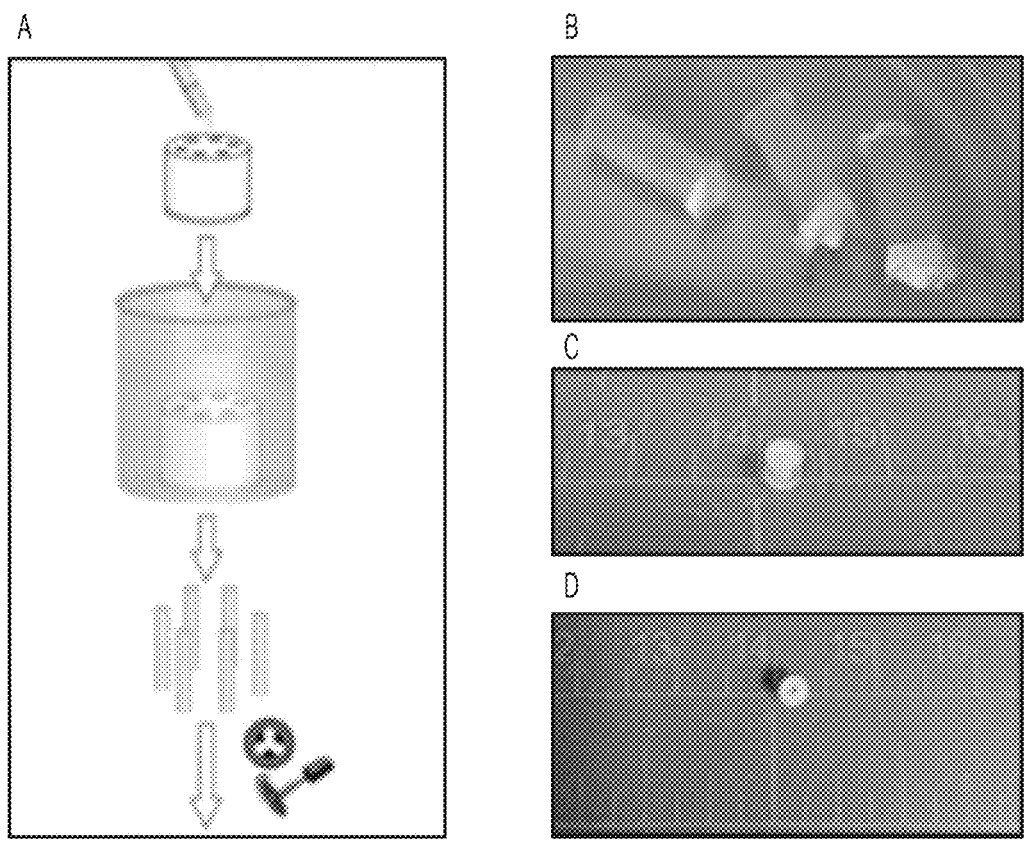
FIG. 3 shows an exemplary provided method for ear tube fabrication. (panel A) shows a schematic for producing ear tubes via a provided injection molding process. Following fabrication steps of injection, freeze-drying, methanol treatment, drying (panel B) and machining, tubes were fabricated (shown in side-view (panel C), and top view (panel D)). (panel E) SEM images show a low degree of porosity in this exemplary embodiment.
Figure 3:
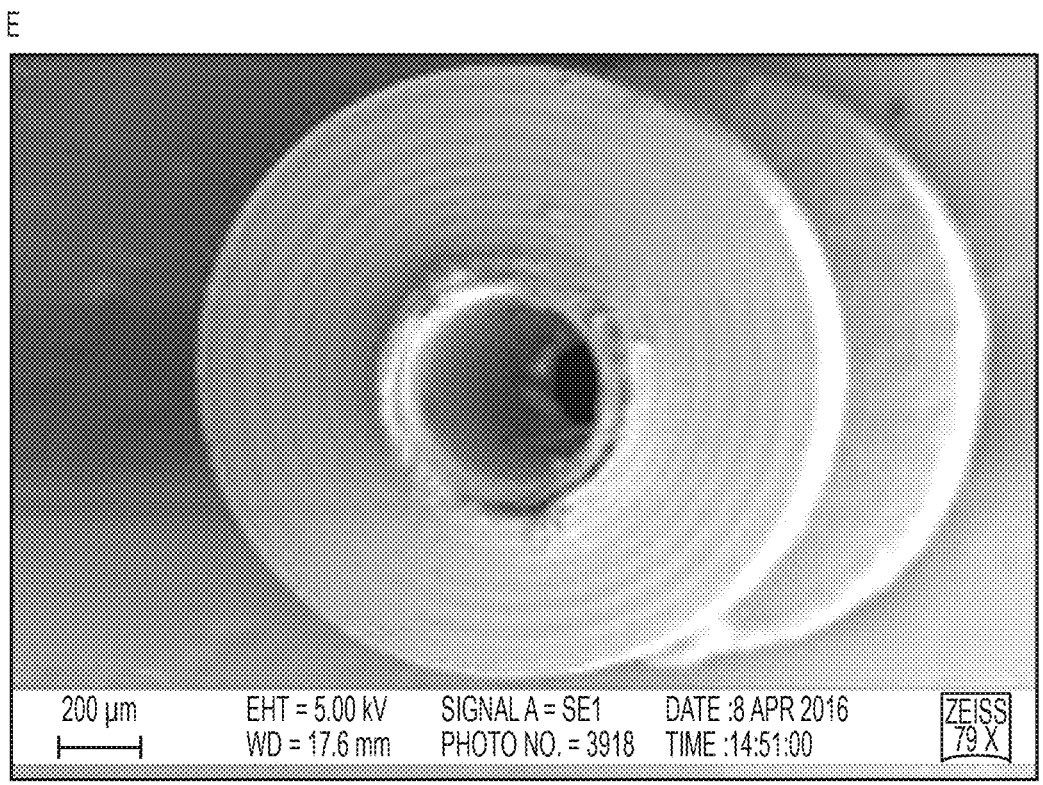
Figure 4:
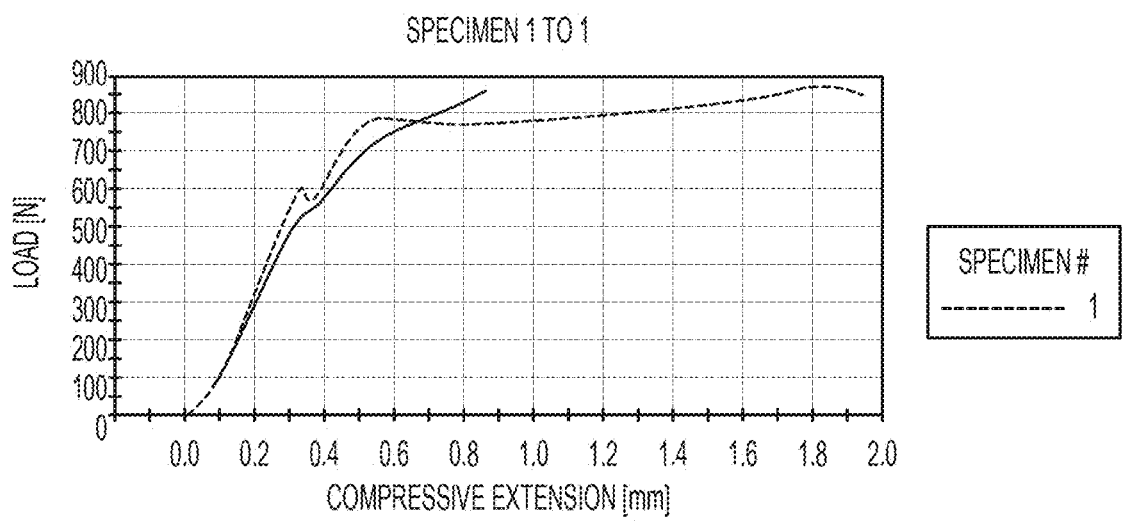
FIG. 4 panel (A) shows the results of Instron mechanical testing was performed and compressive modulus was calculated for exemplary ear tubes shown in FIG. 3 (shown in FIG. 3, panels C, D, and E). Panel (B) exemplary compressive modulus is shown, panel (C) as is the compressive modulus of the current PTFE tubes on the market, which is much less than the silk bone screws that are fabricated using a similar method (panel C).

The molds were then placed in a methanol bath for 12 hours (FIG. 3, panel A), washed in deionized (DI) water, and allowed to air dry prior to machining. It is important to note that in some embodiments, injected samples may go directly into methanol without the intervening lyophilization step. The machined tubes had an inner diameter of 0.8 mm, outer diameter of 2 mm and length of 1.7 mm, which were measured using ImageJ software of scanning electron microscopy images (SEM) (FIG. 3, panel E). In some embodiments, the dimensions could be adjusted, such as to 0.79 mm inner diameter and 1.36 mm outer diameter. However, in some embodiments, sterilization techniques such as autoclaving may cause the tube to shrink, so this reduction in size should be accounted for prior to machining to a different dimension. Drying in a 60° C. oven may be used, in some embodiments, to reduce shrinking, and/or the silk ear tube may be designed to take the shrinking into account. In this Example, a collar-button flange was used, though in other embodiments, other designs may be useful, for example, a pop-beveled grommet. In the illustrated embodiment, the tube includes a first flange on a first end of the body and a second flange on a second end of the body opposite the first end. Two of the silk ear tubes were subjected to Instron mechanical testing to gauge the mechanics of tubes produced with this method. As shown in FIG. 4, panels A and B, the compressive moduli of the tubes were between 624 and 717 MPa, which is in line with commercialized PTFE tube mechanics and much lower than screws that are produced using a similar approach (FIG. 4, panel C).

In addition, sample silk ear tubes produced as described above were dried using a) a bench top lyophilizer which did not simultaneously freeze the sample while on vacuum, b) methanol treatment while timing, and c) large batch silk concentration methods.

Figure 5:
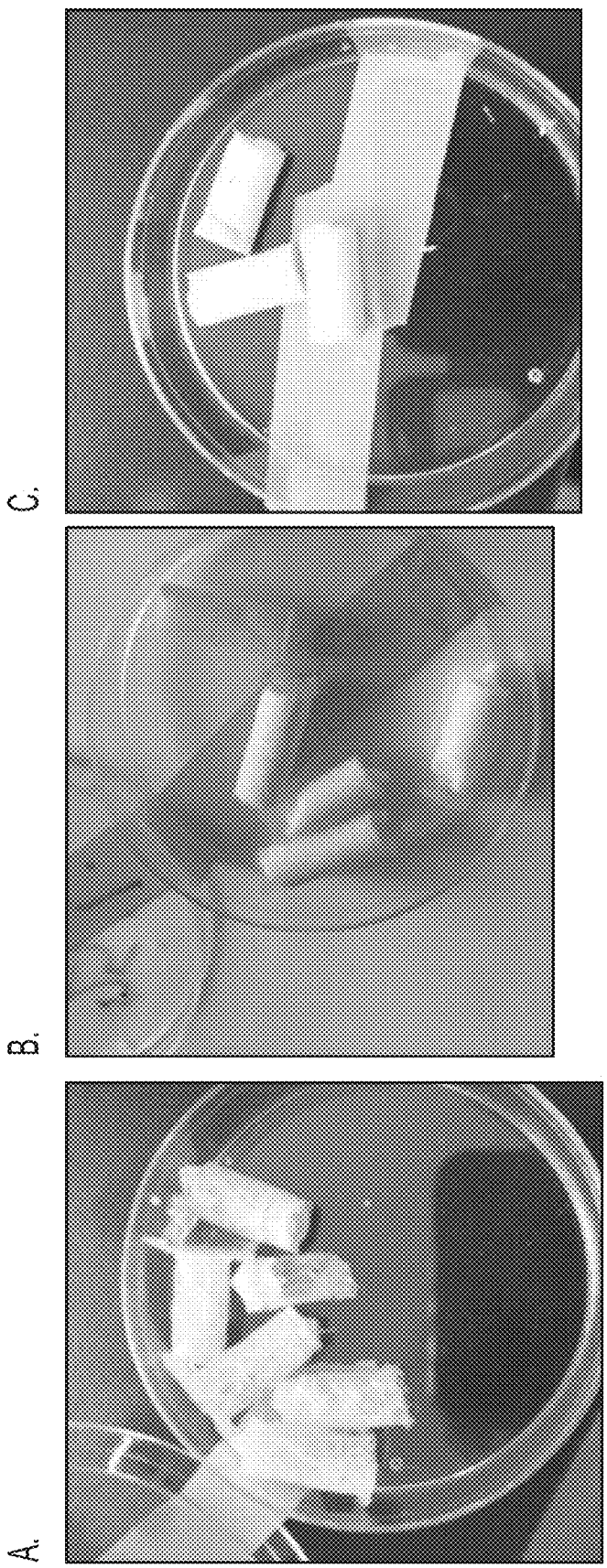
FIG. 5 shows (panel A) results of bench top lyophilization of exemplary ear tubes, (panel B) and (panel C) show exemplary methanol-based dehydration of provided ear tubes for 6 hours at a temperature between −20° C. and −30° C. with (panel B) showing the results for ear tubes made with a 25% silk fibroin solution and (panel C) showing the results for ear tubes made with a 33% silk fibroin solution.

Without wishing to be held to a particular theory, it appears that the molds used in this Example require a lyophilizer that can dry the samples in vacuum, while maintaining a temperature between −20 and −30° C. to ensure the samples remains frozen during the drying process. Placing the sample in the bench-top lyophilizer resulted in partially defrosted tubes during the drying process (FIG. 5, panel A). Further, methanol treatment was performed for 6 hours, and this methanol treatment time resulted in a tube that resembled more of a styro-foam material (see FIG. 5, panels B and C), rather than the mechanically superior material revealed from steps that achieve the tube shown in FIG. 3. The mechanics were not tested on the tubes with shorter methanol time, as they lacked the ability to be machined. In some embodiments, therefore, it may be advantageous to administer methanol treatment for at least 12 hours to encourage additional β-sheet formation. Additionally, large-batch silk concentration methods were experimented with, where silk with 5-7 w/v % was added to dialysis tubing and placed in a hood for 1 day to pre-concentrate the silk, prior to placement and concentration in 2 mL tubes in the CentriVap machine. According to some embodiments, the transition to larger batch concentration methods may allow for larger quantities of silk to be recovered post-CentriVap spinning, helping to ensure enough silk is extruded from the 2 mL tubes to reduce air bubble accumulation in subsequent injection steps.

Scanning electron microscope (SEM) imaging of the exemplary ear tubes produced in this Example revealed a very low degree of porosity. Without wishing to be held to a particular theory, a higher degree of porosity may be desirable for some embodiments, for example, for biodegradable drug-eluting silk ear tubes. Although porosity was minimal, the exemplary technique of this Example provides a reproducible, scalable, machinable, and more reliable drug-loading method than previously observed.

This Example shows, inter alia, that silk ear tubes having mechanical characteristics similar to currently marketed PTFE ear tubes may be produced in a rapid and economical manner. It also shows that these tubes may be further customized to suit a particular application or even a particular subject.

Example 3—Exemplary Production of Porous Silk Ear Tubes Via Aqueous Process

Preparation of silk solution—Silk solution may be generated from *Bombyx mori* silkworm cocoons according to the procedures described in previous studies. Cocoons of *B. mori* silkworm silk can be supplied by Tajima Shoji Co (Yokohama, Japan). Briefly, the cocoons are degummed in a boiled 0.02 M $Na_2CO_3$ (Sigma-Aldrich, St Louis, Mo.) solution for 30 min to provide a 5-7% w/v silk solution. Solutions were then allowed to concentrate for 1 day to a solution of approximately 8-9% w/v silk. Subsequently, silk solutions were further concentrated using a CentriVAP vacuum concentrator to achieve silk solutions with a concentration of silk between 20-25% w/v.

Preparation of Silk tubes—the concentrated silk solutions described above were then injected into 1 mL wax molds, and the molds were then placed in a methanol bath for 48 hours. After 48 hours, silk cylinders were removed from the mold and placed in a beaker of deionized water (DI) and stirred for 24 hours. Then, the washed silk cylinders were removed from the molds and placed into 1 mL wax molds to dry in a hood. Without wishing to be held to a particular theory, it is contemplated that drying the silk cylinders in a mold may help to avoid warping of material during the drying process. After drying, the silk cylinders were machined to the desired ear tube dimensions.

Coating Tubes with Silk and Polyethylene Oxide (PEO)

PEO solution preparation—a 6% wt solution of PEO was prepared by adding 60 mg/mL of Poly(ethylene) Oxide (PEO) to 50 mL of deionized (DI) water (total of 300 mg of PEO). The DI water was heated on a hot plate with a stir bar at about 80° C. for 10 minutes before adding PEO. Once the PEO was added to the DI water, the mixture was stirred for an hour and became a viscous, homogenous solution. Concurrently, a 20% w/v silk solution was prepared.

Figure 6:
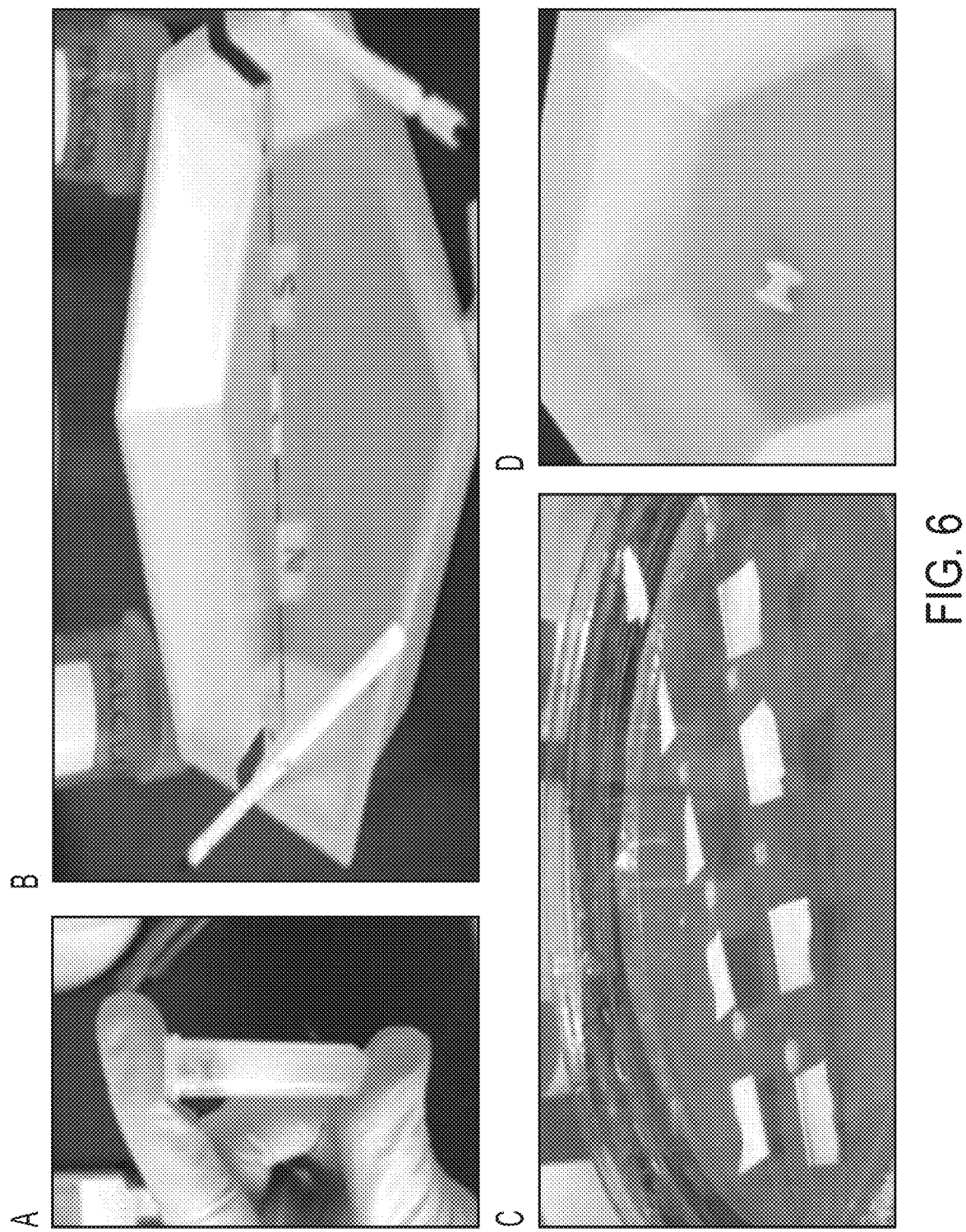
FIG. 6 shows exemplary photographs of a provided coating process that includes steps of mixing a PEO/silk solution (panel A), painting the coating on with a paintbrush (panel B), methanol treating (panel C), and drying (panel D) to achieve an ear tube with a porous coating.

Preparation of coating solution and coating/induction of pore formation of coating on silk tubes—Next, an 80/20 w/w mixture of silk/PEO was made by calculating the volume of silk and PEO to mix as follows:

Using 1 mL of 20% silk:
a. (x total mg)*0.8=200 mg of silk
b. x total=250 mg, so mg of PEO=250 mg total−200 mg silk=50 mg PEO
c. 50 mg PEO/(60 mg/mL PEO)=0.83 mL of PEO After adding the silk and PEO volumes to a 2 mL eppendorf tube, the mixture was stirred with a needle and then vortexed until the solution was completely mixed. Next, and prior to coating the silk tubes: the tubes were placed on a polytetrafluoroethylene (PTFE) coated rod with a diameter of 0.79 mm with the silk tubes spaced evenly. To ensure minimal movement of tubes while PEO/silk solution is painted on, tape was placed on either side of each of the tubes, which also prevented coated tubes from sliding into each other (see FIG. 6). Next, the rod was placed on a weigh boat and a touchup paint brush was used to apply an even layer of the silk/PEO solution onto each tube (see FIG. 1, panel B). Then, immediately after coating, 100% methanol was poured into a dish and the tubes were allowed to sit horizontally therein for 1 hour, where β-sheet formation occurred in the silk and the PEO was highly soluble, creating a porous coating on the outside of the ear tube. Approximately one hour after placement into the methanol bath, the tubes were placed in DI water in a Falcon tube and shaken for 48 hours. After shaking, the tubes were removed from the water and allowed to dry for 24 hours in a fume hood.

Figure 7:
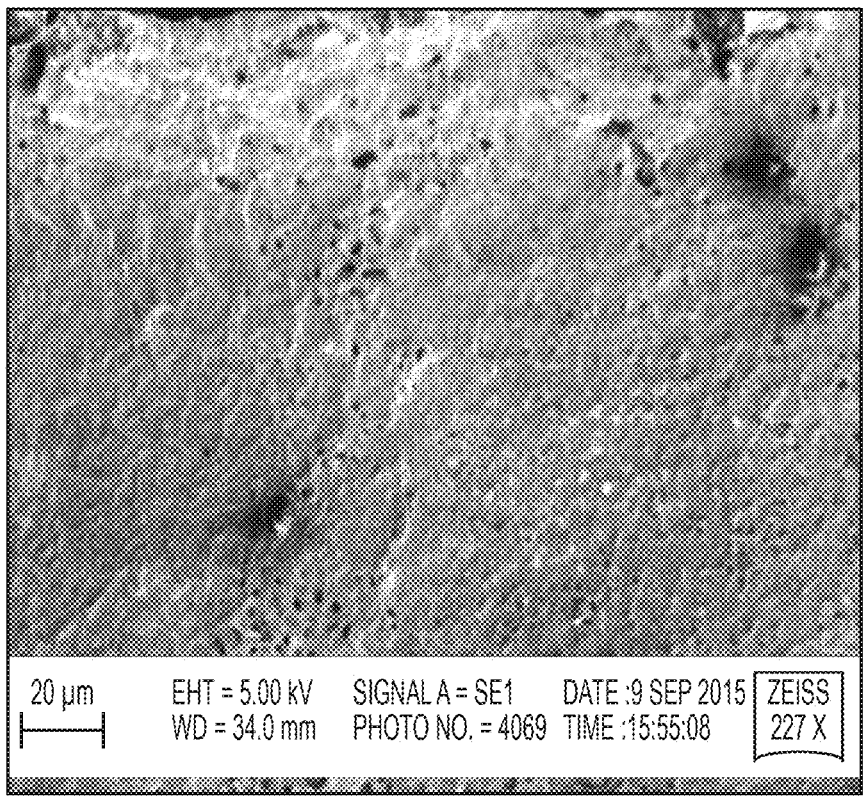
FIG. 7 shows exemplary photographs of certain provided compositions made in accordance with the methods shown in FIG. 6, including a PEO coating on ear tube, which provides a porous layer for, inter alia, tympanic membrane attachment and degradation.
Figure 7:
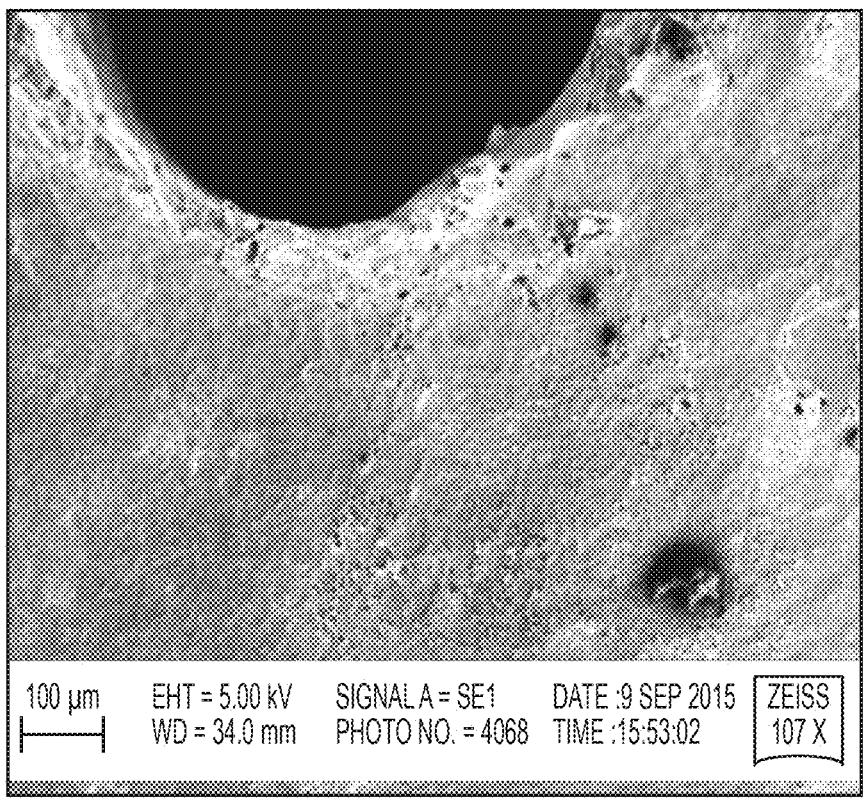
Figure 7:
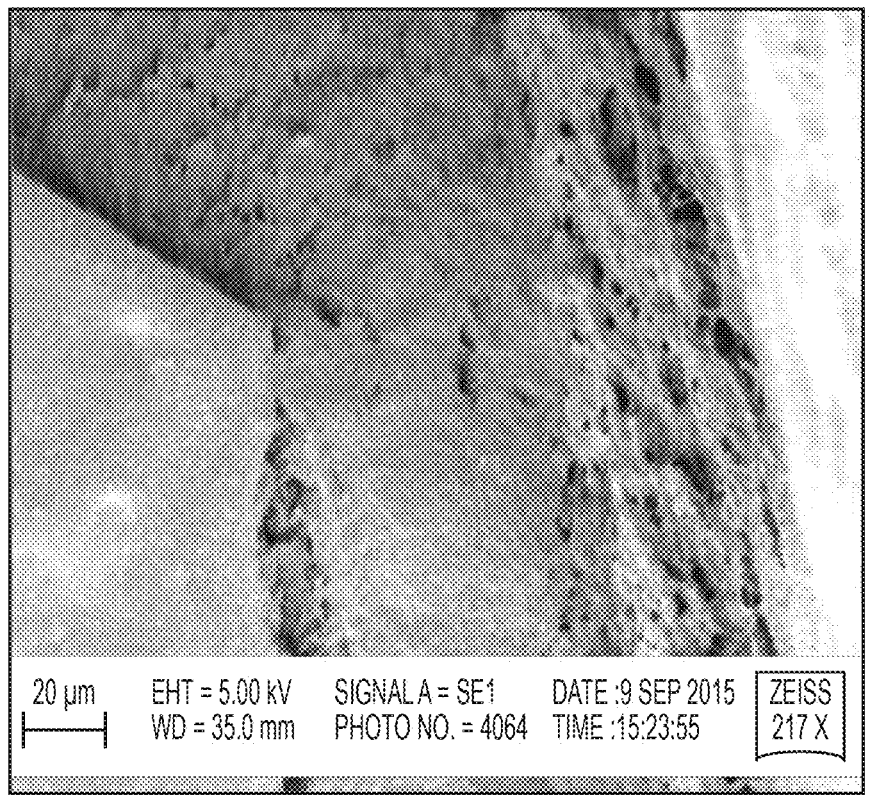
Figure 7:
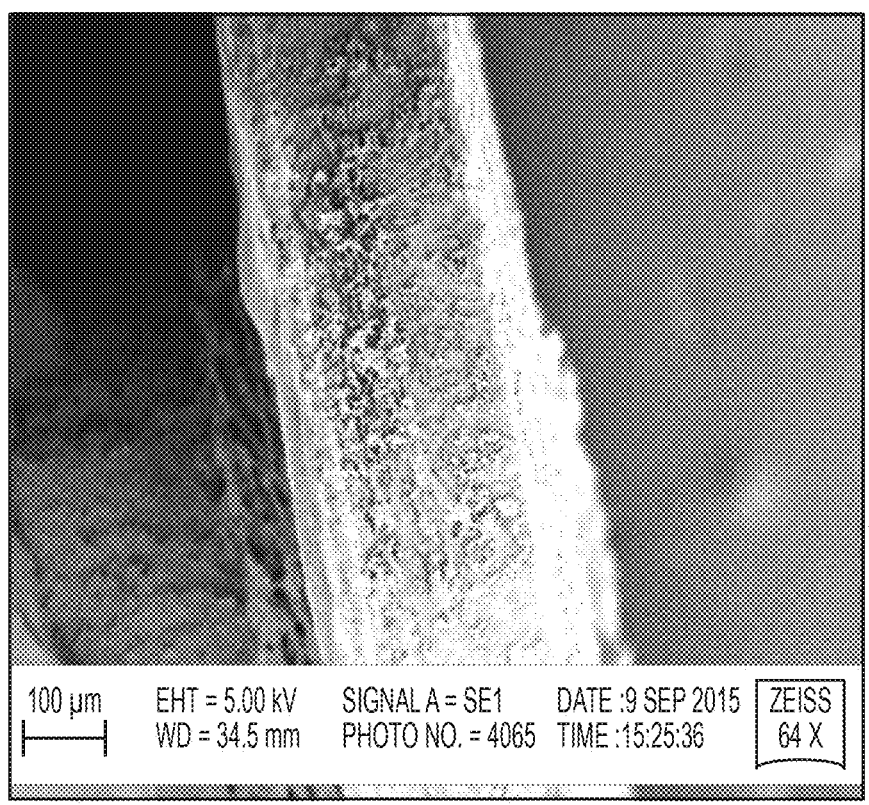
Figure 8:
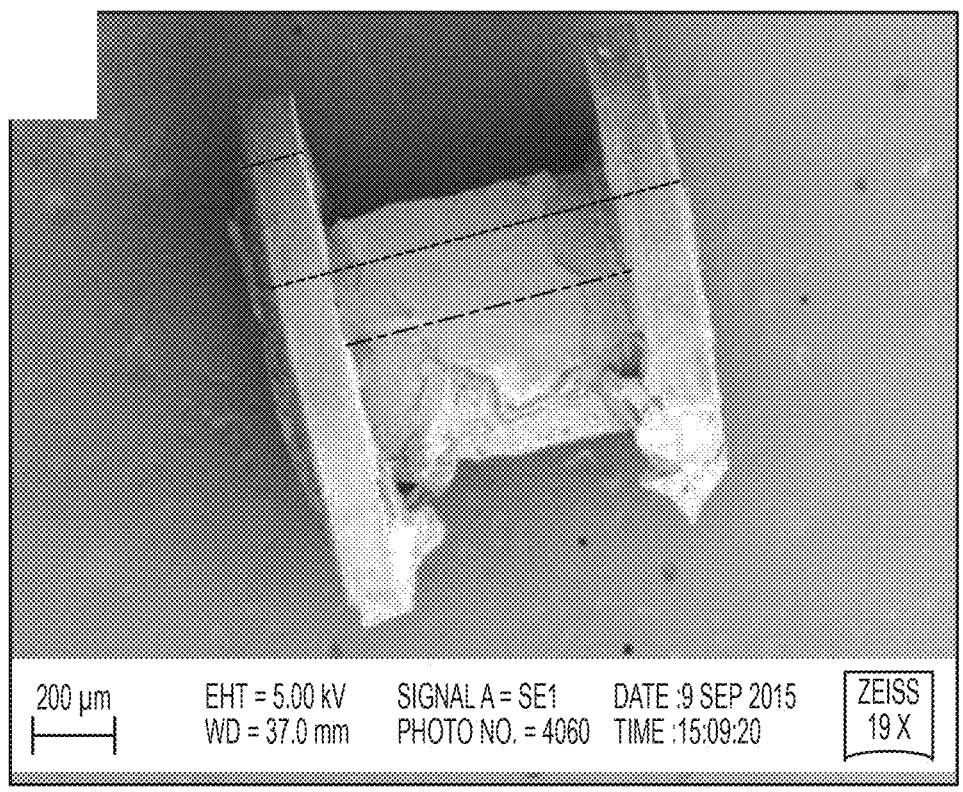
FIG. 8 shows exemplary images and dimensions of certain provided embodiments shown in FIG. 7 as measured in ImageJ software post-sterilization (inner diameter was adjusted to 1.1 mm).
Figure 8:
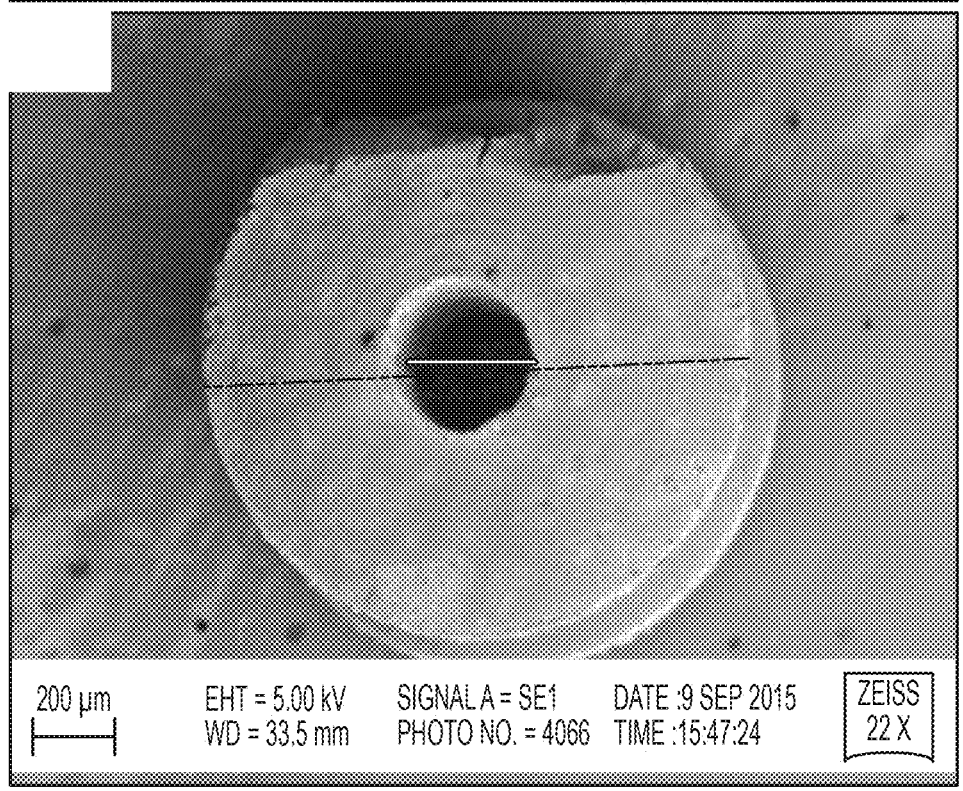

After drying, the silk tubes were autoclaved and examined using scanning electron microscopy (SEM). As is shown in FIGS. 7-8, provided methods are able to provide porous silk ear tubes. Specifically, FIG. 7 shows a plurality of pores present in tubes produced in this Example. Without wishing to be held to a particular theory, it is contemplated that the presence and nature of these pores may facilitate tympanic membrane attachment and/or degradation of the tubes in vivo after a period of time. FIG. 8 shows exemplary SEM photographs of tubes provided in this Example, including views of the significant degree of porosity achievable via provided methods.

Example 4—Coating Tubes with Silk and Ciprofloxacin

Coating of porous tubes with Ciprodex (exemplary active agent)—9 mg/mL ciprofloxacin HCL and 3 mg/mL dexamethasone were added to a silk solution concentrated to between 20-25% silk w/v. Next silk tubes prepared as described above in Example 3, without the PEO coating, were placed on a Teflon rod. The silk tubes and Teflon rod were then dipped into the silk-ciprofloxacin-dexamethasone solution and then placed horizontally in a weigh boat filled with 100% methanol for 1 hour. Importantly, the methanol bath was saturated with both ciprofloxacin and dexamethasone to prevent drug release from the silk-drug dip coat into the methanol solution. After methanol treatment, the silk tubes were dried in a fume hood. Subsequent to drying, the silk tubes were sterilized using ethylene oxide sterilization.

Figure 9:
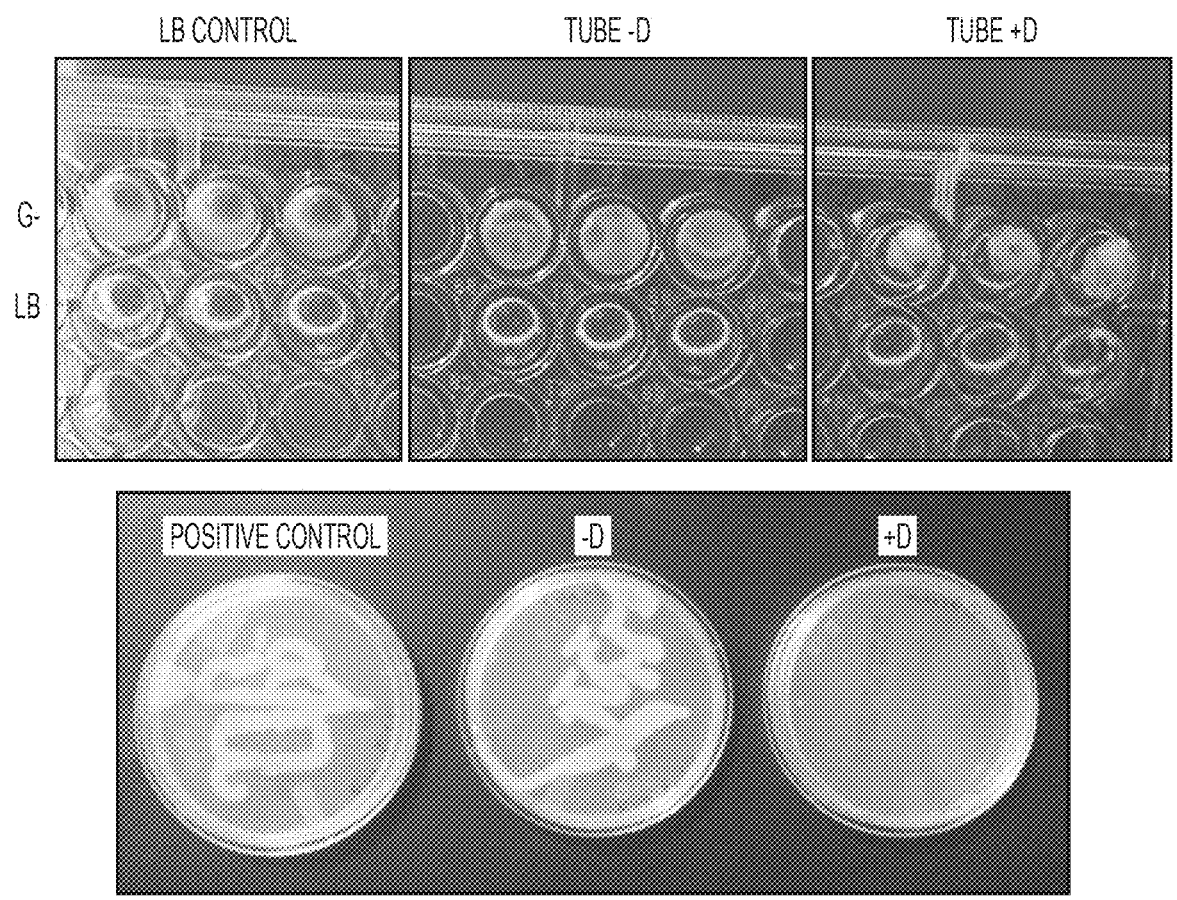
FIG. 9 shows exemplary results relating to the efficacy of certain drug eluting tubes via dip coating method post-incubation in 37° C. for 24 hours with $5.21*10^7$ CFU/mL of gram negative *Moraxella catarrhalis* bacterial strain (top row). As is shown in the top row of FIG. 9, exemplary provided silk ear tubes coated with coated drug (Tube +D), show antimicrobial activity compared to a similar tube without a drug coating (Tube −D) and positive control of lysogeny broth with gram negative bacteria (LB, G−). Subsequent culture of media for an additional 24 hours shows the drug eluting tube was effective at both preventing growth and killing the bacteria (bottom row, right) compared to the tube without drug (bottom row, middle) and the positive control (bottom row, left).

To test the effectiveness of provided silk ear tubes coated with at least one active agent, here ciprofloxacin and dexamethasone, these drug coated silk tubes were compared against silk ear tubes with no such coating and also against a positive control containing lysogeny broth in the ability to prevent and/or slow the growth of bacteria. To test this, each of the drug coated silk ear tubes, non-drug coated silk ear tubes, and positive control ear tubes were incubated with approximately 5.21*107 CFU/mL of the gram negative bacteria *Moraxella catarrhalis* for 24 hours in a multi well plate (see FIG. 9 top row). After approximately 24 hours, the media was removed from the multi-well plate and incubated at 37° C. on a culture plate for an additional 24 hours. FIG. 9 shows that the drug coatings were effective in reducing and/or preventing the growth of bacteria for at least 24 hours.

As shown in these Examples, provided methods may be sued to create any of a variety of silk ear tubes. In some embodiments, provided silk ear tubes may include physical and/or mechanical characteristics similar to that of previously known, non-silk ear tubes, while being biodegradable and amenable to including one or more active agents, such as in a coating or in pores of a provided embodiment.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

The invention claimed is:

1. A resorbable silk ear tube comprising:
   a body made from silk fibroin for placement within an ear canal of a subject, the body provided with a compressive modulus from about 482 MPa to about 2170 MPa, wherein the compressive modulus is suitable for use as an ear tube in a human subject;
   a length of at least about 0.4 mm with an outer diameter of at least 0.08 mm; and
   a lumen extending along the body.

2. The resorbable silk ear tube of claim 1, further comprising a first flange on a first end of the body and a second flange on a second end opposite the first end.

3. The resorbable silk ear tube of claim 1, wherein the resorbable silk ear tube is porous.

4. The resorbable silk ear tube of claim 1, wherein the resorbable silk ear tube comprises two or more layers.

5. The resorbable silk ear tube of claim 4, wherein each of the two or more layers defines a thickness of between about 1 nm and 1 mm.

6. The resorbable silk ear tube of claim 4, wherein at least one of the two or more layers defines a thickness that is different from at least one other layer.

7. The resorbable silk ear tube of claim 4, wherein a thickness of any one of the two or more layers is based on a concentration of fibroin in the silk fibroin solution.

8. The resorbable silk ear tube of claim 4, wherein at least one of the two or more layers comprises at least one therapeutic agent.

9. The resorbable silk ear tube of claim 8, wherein the at least one therapeutic agent is selected from the group consisting of antibiotics, pain relievers, and steroids.

10. The resorbable silk ear tube of claim 1, wherein the resorbable silk ear tube further comprises at least one protease.

11. The resorbable silk ear tube of claim 1, wherein the body is formed from a silk fibroin solution containing between 1%-30% wt silk fibroin.

12. The resorbable silk ear tube of claim 1, wherein the resorbable silk ear tube has a resorption rate of between one day and one week, inclusive.

13. The resorbable silk ear tube of claim 1, wherein the resorbable silk ear tube has a resorption rate of between eight days and 2 years, inclusive.

14. The resorbable silk ear tube of claim 1, wherein the resorbable silk ear tube comprises beta-sheet content between 1-60%.

15. The resorbable silk ear tube of claim 1, wherein the silk fibroin is selected from the group consisting of spider silk, silkworm silk, and recombinant silk.

16. The resorbable silk ear tube of claim 1, wherein the body has a compressive modulus from about 624 MPa to about 717 MPa.

17. A resorbable silk ear tube comprising:
   a body made from silk fibroin for placement within an ear canal of a subject, wherein the body has a compressive modulus from about 624 MPa to about 717 MPa;
   a length of at least about 0.4 mm with an outer diameter of at least 0.08 mm; and
   a lumen extending along the body.

* * * * *